(12) United States Patent
Marion et al.

(10) Patent No.: US 8,981,128 B2
(45) Date of Patent: Mar. 17, 2015

(54) PROCESS FOR PRODUCING COMPOUNDS COMPRISING NITRILE FUNCTIONS

(75) Inventors: Philippe Marion, Vernaison (FR);
Roland Jacquot, Francheville (FR)

(73) Assignee: Rhodia Operations, Paris (FR)

( * ) Notice: Subject to any disclaimer, the term of this patent is extended or adjusted under 35 U.S.C. 154(b) by 0 days.

(21) Appl. No.: 14/131,453

(22) PCT Filed: Jul. 5, 2012

(86) PCT No.: PCT/EP2012/063093
§ 371 (c)(1),
(2), (4) Date: Jan. 15, 2014

(87) PCT Pub. No.: WO2013/007586
PCT Pub. Date: Jan. 17, 2013

(65) Prior Publication Data
US 2014/0171663 A1 Jun. 19, 2014

(30) Foreign Application Priority Data
Jul. 8, 2011 (FR) ...................... 11 56222

(51) Int. Cl.
*C07D 307/68* (2006.01)
*C07D 211/02* (2006.01)
*C07D 211/88* (2006.01)
*C07D 307/24* (2006.01)
*C07D 307/54* (2006.01)

(52) U.S. Cl.
CPC ............ *C07D 307/68* (2013.01); *C07D 211/02* (2013.01); *C07D 211/88* (2013.01); *C07D 307/24* (2013.01); *C07D 307/54* (2013.01)
USPC ....................................... 549/414

(58) Field of Classification Search
CPC .. C07D 211/02; C07D 211/88; C07D 307/24; C07D 307/68
USPC .......................................... 549/474
See application file for complete search history.

(56) References Cited

U.S. PATENT DOCUMENTS
2013/0204001 A1  8/2013  Jacquot et al.

FOREIGN PATENT DOCUMENTS
FR  1525498 A  5/1968
GB  722843 A  2/1955
WO  2011144619 A1  11/2011

OTHER PUBLICATIONS

David A. Klein (J. Org. Chem. (1971) vol. 36 (20); pp. 3050-3051).*
David A. Klein: "Nitrile synthesis via the acid-nitrile exchange reaction", The Journal of Organic Chemistry, vol. 36, No. 20, Oct. 1, 1971, pp. 3050-3051, XP055014514, ISSN: 0022-3263, DOI: 10.1021/jo00819a035.

* cited by examiner

Primary Examiner — Kristin Vajda
Assistant Examiner — Valerie Rodriguez-Garcia

(57) ABSTRACT

The present invention relates to the production of compounds comprising nitrile functions and of cyclic imide compounds. It relates more particularly to the production of compounds comprising nitrile functions from compounds comprising carboxylic functions, advantageously of natural and renewable origin, and from 2-methylglutaronitrile (MGN) or a mixture N of dinitriles comprising 2-methylglutaronitrile (MGN), 2-ethylsuccinonitrile (ESN) and adiponitrile (AdN).

20 Claims, No Drawings

PROCESS FOR PRODUCING COMPOUNDS COMPRISING NITRILE FUNCTIONS

This application is a U.S. national phase entry under 35 U.S.C. §371 of International Application No. PCT/EP2012/063093, filed on Jul. 5, 2012, which claims priority to French Application No. 1156222, filed on Jul. 8, 2011, the entirety of which is being incorporated herein by reference for all purposes.

The present invention relates to the manufacture of compounds comprising nitrile functional groups and of cyclic imide compounds.

It relates more particularly to the manufacture of compounds comprising nitrile functional groups from compounds comprising carboxyl functional groups, advantageously of natural and renewable origin, and from a mixture N of dinitriles comprising 2-methylglutaronitrile (MGN), 2-ethylsuccinonitrile (ESN) and adiponitrile (AdN).

Compounds comprising nitrile functional groups are important products for the manufacture of amine compounds. Dinitrile compounds result in amines which are, for example, monomers which are the source of polymers, such as polyamide, for example. Mononitrile compounds result in amines or in amides which are, for example, used for the manufacture of cationic surfactants.

Many processes for the synthesis of nitriles have been provided, in particular synthesis processes starting from ammonia and from carboxylic acids. These processes mainly use, as starting raw material, hydrocarbon compounds resulting from oil refining, and ammonia, which is obtained from hydrogen originating from steam reforming processes, which consume gas and energy.

Given that oil resources are running out, many research studies are being undertaken in order to develop processes for the synthesis of these compounds, which are important in the manufacture of materials used in numerous applications, from raw materials or resources termed renewable, or from recycled raw materials, which are normally destroyed or given added value only in the form of energy. These renewable resources can be produced from cultivated or non-cultivated vegetable matter, such as trees, plants, for example sugarcane, corn, cassava, wheat, rape, sunflower, palm, castor oil plant or the like.

This vegetable matter is converted by processes generally comprising several mechanical, chemical and biological stages.

Moreover, with regard to the recycled raw materials, the manufacture of adiponitrile, a major chemical intermediate used in particular in the synthesis of hexamethylenediamine and caprolactam (monomers for the manufacture of polyamides), obtained by hydrocyanation of butadiene, generates a stream of dinitrile by-products predominantly comprising branched dinitrile compounds, such as 2-methylglutaronitrile or 2-ethylsuccinonitrile. This mixture of branched dinitrile compounds is obtained by distillation in order to separate it from the adiponitrile. As the separation is not generally complete, the mixture of branched dinitrile compounds can also comprise a small proportion of adiponitrile.

Several solutions have been provided for giving added value to these by-products or mixtures. One of these consists in hydrogenating the dinitrile compounds to give primary amines, in particular for producing 2-methylpentamethylenediamine (MPMD), used as monomer in the manufacture of specific polyamides or as intermediate in the production of vitamin B3 (nicotinamide). This process requires stages of purification of the 2-methylglutaronitrile and the 2-methylpentamethylenediamine.

Industrially, these by-products are also made use of economically in the form of vapor or energy by combustion. However, this combustion can require treatment of the gases in order to remove the nitrogen oxides produced and it produces carbon dioxide gas which is discharged to the atmosphere.

There thus exists a considerable demand and need to find new routes for giving added value to and converting these dinitrile compounds or mixtures into chemical compounds which can be given added value and which are economically advantageous.

To this end, the invention provides a process for the preparation of at least one nitrile of general formula I

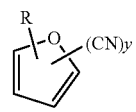

or respectively of at least one nitrile of general formula III

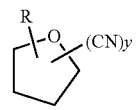

and of at least the cyclic imide 3-methylglutarimide,
by reaction between at least one carboxylic acid of general formula II

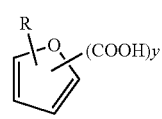

or respectively at least one carboxylic acid of general formula IV

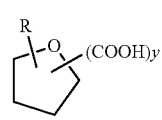

and at least 2-methylglutaronitrile (MGN),
with
y is equal to 1 or 2
R represents a hydrogen atom or one or more substituents.

Advantageously, a mixture N of dinitriles comprising 2-methylglutaronitrile (MGN), 2-ethylsuccinonitrile (ESN) and adiponitrile (AdN) is employed. At least the cyclic imides 3-methylglutarimide and 3-ethylsuccinimide are then obtained.

Preferably, the mixture N of dinitriles is a mixture resulting from the process for the manufacture of adiponitrile by double hydrocyanation of butadiene. It preferably corresponds to the distillation fraction which makes it possible to separate the branched dinitriles (2-methylglutaronitrile, 2-ethylsuccinonitrile) from adiponitrile.

This mixture of dinitriles generally has the following composition by weight:

2-Methylglutaronitrile: between 70% and 95%, preferably between 80% and 85%,

2-Ethylsuccinonitrile: between 5% and 30%, preferably between 8% and 12%,

Adiponitrile: between 0% and 10%, preferably between 1% and 5%, the remainder to 100% corresponding to various impurities.

The process of the invention uses a carboxylic acid of general formula II as described above.

Advantageously, the carboxylic acid of general formula II or IV results from a renewable material of vegetable origin.

A renewable material or resource is a natural, animal or plant, resource, the stock of which can be reconstituted over a short period on the human timescale. It is in particular necessary for this stock to be able to be renewed as quickly as it is consumed.

Unlike materials resulting from fossil materials, renewable raw materials contain a high proportion of $^{14}C$. Preferably, the nitriles of the invention consist of organic carbon resulting from renewable raw materials. Thus, this preferred characteristic might be certified by determining the $^{14}C$ content according to one of the methods described in the standard ASTM D6866, in particular according to the mass spectrometry method or the liquid scintillation spectrometry method which are described in this standard.

These renewable resources can be produced from cultivated or non-cultivated vegetable matter, such as trees, plants, for example sugarcane, corn, cassava, wheat, rape, sunflower, palm, castor oil plant or the like.

For example, the carboxylic acid of general formula II or IV can result from renewable resources, such as natural polysaccharides, such as, for example, starch or cellulose, it being possible for the starch to be extracted, for example, from corn, wheat or potato. It can in particular originate from various conversion processes, in particular conventional chemical processes, enzymatic conversion processes or fermentation conversion processes.

2,5-Furandicarboxylic acid can, for example, be obtained from mucic acid or from hydroxymethylfurfural.

Advantageously, R is chosen from:
linear or branched alkyl groups preferably having from 1 to 6 carbon atoms and more preferentially still from 1 to 4 carbon atoms,
linear or branched mono-, poly- or perhalogenated alkyl groups preferably having from 1 to 6 carbon atoms and from 1 to 13 halogen atoms and more preferably still from 1 to 4 carbon atoms and from 1 to 9 halogen atoms,
ether $R_2$—O— or thioether $R_2$—S— groups in which $R_2$ represents a linear or branched alkyl group having from 1 to 6 carbon atoms and more preferably still from 1 to 4 carbon atoms or the phenyl group,
acyloxy or aroyloxy $R_2$—CO—O— groups in which the $R_2$ group has the meanings given above,
acyl or aroyl $R_2$—CO— groups in which the $R_2$ group has the meanings given above,
the hydroxyl group,
a halogen atom, preferably a fluorine atom.

According to a specific embodiment of the invention, y is equal to 1 and R represents —CO—O—$R_3$ with $R_3$ which represents an alkyl group having from 1 to 4 carbon atoms in the general formula II or IV.

Preferably, the compound of formula II or IV is chosen from 2,5-furandicarboxylic acid, 2,5-tetrahydrofurandicarboxylic acid, 2-furoic acid, 2,5-furandicarboxylic acid monomethyl ester or 2,5-tetrahydrofurandicarboxylic acid monomethyl esters.

The compound of formula IV, when it is a diacid (y=2) or a compound comprising an acid functional group and an ester functional group (y=1 and R represents —CO—O—$R_3$ with $R_3$ which represents an alkyl group having from 1 to 4 carbon atoms in the general formula IV), can be employed in the reaction of the invention in the form of just one isomer (for example, the cis isomer or the trans isomer) or in the form of a mixture of isomers (for example, a mixture of the cis isomer and the trans isomer). By way of illustration, when the compound of formula IV is 2,5-tetrahydrofurandicarboxylic acid, it can be employed in the form of the trans isomer, of the cis isomer or of a mixture of the cis isomer and the trans isomer.

In the context of the process of the invention, use may be made of a mixture of several carboxylic acids, for example a carboxylic acid of general formula II or IV and another carboxylic acid, or a mixture of several carboxylic acids of formula II or IV.

The process of the invention is advantageously carried out at a temperature of between 150 and 350° C. The pressure used is generally between atmospheric pressure and a few bar.

Catalysts can be used in the context of the process of the invention. Mention may be made, by way of example of catalysts, of phosphoric acid, phosphates, borophosphates, sulfuric acid, sulfonic acid, benzenesulfonic acid, toluenesulfonic acids, such as para-toluenesulfonic acid, naphthalenesulfonic acids, silica, alumina, clay or silica/alumina.

Advantageously, an amount of 2-methylglutaronitrile (MGN) or of mixture N is used such that at least one molecule of 2-methylglutaronitrile (MGN) or of 2-ethylsuccinonitrile (ESN) is introduced into the reaction medium, per acid functional group of the carboxylic acid of general formula II or IV to be converted into nitrile functional group.

When a diacid is used as acid of general formula II or IV, it is possible to obtain the corresponding dinitrile or the corresponding acid nitrile (for example, by using a deficiency of nitrile functional group).

During the reaction between the compound of formula (II) or (IV) and the mixture N of dinitriles in accordance with the invention, imides are formed, in particular 3-methylglutarimide, resulting from MGN, and 3-ethylsuccinimide, resulting from ESN.

Advantageously, the process of the invention also comprises a stage of recovery, on the one hand, of at least the nitrile of formula (I) or (III) and, on the other hand, of at least the cyclic imide, from the reaction medium.

This recovery can be carried out by separation of the compounds of the reaction medium, according to any known method, such as distillation.

According to a first advantageous embodiment, the compounds can be obtained by reactive distillation. This is because, when the nitrile of formula (I) or (III) which it is desired to obtain has a boiling point below that of the reaction temperature (which is in particular the case for nitriles having a low carbon number), this nitrile can be distilled as it is formed, thereby shifting the equilibrium of the reaction toward the formation of this nitrile; this is therefore particularly advantageous. This reactive distillation method can, for example, be used when the nitrile of formula (I) or (III) is 2,5-dicyanotetrahydrofuran or a mononitrile.

According to a second advantageous embodiment, the compounds can be separated by extraction with hot water. This is because imides are generally soluble in water, unlike in particular nitriles, which allows good separation via a route which is easy to implement. This route is to be favored in particular when the nitriles and the imides to be separated have boiling points which are close and when they are consequently difficult to separate by conventional distillation, for example. The temperature of the water during this extraction is generally greater than or equal to 50° C.

According to a specific embodiment of the invention, the nitrile of formula (I) or (III) thus recovered is hydrogenated in order to form the corresponding amine, according to a method known to a person skilled in the art. When a nitrile of formula (I) is recovered, its hydrogenation can result in the amine corresponding to the compound of formula (III), by hydrogenation not only of the nitrile functional group but also by hydrogenation of the double bonds of the furan ring. An amine is thus obtained, all the carbons of which are bio-based (as resulting from a bio-based carboxylic acid, that is to say a carboxylic acid resulting from a renewable raw material) and the nitrogen atoms of which are recycled (as resulting from by-products which are usually incinerated, thereby generating carbon dioxide and nitrogen oxides, which are greenhouse gases which must be treated in order to meet the legislation in force). The diamines can be used as raw materials for the manufacture of polyamides, which will thus be partially or completely bio-based, depending on the acids used for the polymerization. The amines can also be used to prepare surfactants.

According to another specific embodiment of the invention, the cyclic imide recovered according to the process of the invention can be reacted with an alcohol in order to form the corresponding diester. Such a process is known and in particular described in the documents WO 2008/009792 and WO 2009/056477. The diesters can be used as solvents.

Other details or advantages of the invention will become more clearly apparent in the light of the examples given below.

EXAMPLES

Example 1

Preparation of 2,5-dicyanofuran 156 g of 2,5-furandicarboxylic acid and 250 g of 2-methylglutaronitrile (MGN) are introduced into a 500 ml reactor. The reaction medium is stirred and heated, and becomes homogeneous at 275° C. It is maintained under these conditions for 2 h 30. After cooling, the reaction medium is analyzed by GC.
The conversion of the MGN is 25% and the 3-methylglutarimide yield is 18%. The 2,5-dicyanofuran yield is 3%.

Example 2

Preparation of 2,5-dicyanofuran 156 g of 2,5-furandicarboxylic acid, 250 g of 2-methylglutaronitrile (MGN) and 2 g of 85% orthophosphoric acid are introduced into a 500 ml reactor. The reaction medium is stirred and heated, and becomes homogeneous at 275° C. It is maintained under these conditions for 2 h 30. After cooling, the reaction medium is analyzed by GC. The conversion of the MGN is 75% and the 3-methylglutarimide yield is 58%. The 2,5-dicyanofuran yield is 25%.

Example 3

Preparation of cis-2,5-tetrahydrofurandinitrile (THFDN)

40 g of cis-2,5-tetrahydrofurandicarboxylic acid (THFDCA) and 55 g of 2-methylglutaronitrile are introduced into a 250 ml reactor. The reaction mixture is then heated at reflux with stirring. The reaction medium is maintained at 275° C. for 3 h 30. The reaction medium is then analyzed by GC and the following results are obtained:
DC (MGN)=97%
DC (THFDCA)=98%
RY (MGI)=97%
RY (THFDN)=90% cis isomer Example 4

Preparation of a Mixture of cis-+trans-2,5-tetrahydrofurandinitrile isomers 40 g of a cis-+trans-2,5-tetrahydrofurandicarboxylic acid (THFDCA) mixture and 55 g of 2-methylglutaronitrile are introduced into a 250 ml reactor, the two isomers being in the ratio cis/trans=80/20. The reaction mixture is then heated at reflux with stirring. The reaction medium is maintained at 275° C. for 3 h 30. The reaction medium is then analyzed by GC and the following results are obtained:
DC (MGN)=98%
DC (THFDCA)=97%
RY (MGI)=97%
RY (THFDN)=91% cis+trans isomer (ratio cis/trans=80/20)

The invention claimed is:
1. A process for the preparation of at least one nitrile of general formula I

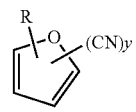

or respectively of at least one nitrile of general formula III

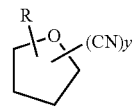

and of at least the cyclic imide 3-methylglutarimide, the process comprising:
reacting at least one carboxylic acid of general formula II

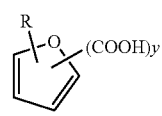

or respectively at least one carboxylic acid of general formula IV

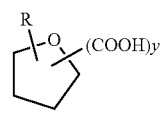

with at least 2-methylglutaronitrile (MGN),
wherein
y is equal to 1 or 2;
R represents a hydrogen atom or one or more substituents.

2. The process according to claim 1, wherein a mixture comprising 2-methylglutaronitrile (MGN), 2-ethylsuccinonitrile (ESN) and adiponitrile (AdN) is employed.

3. The process according to claim 2, wherein the mixture is a mixture resulting from the process for the manufacture of adiponitrile by double hydrocyanation of butadiene.

4. The process according to claim 2, wherein the mixture has the following composition by weight:
2-Methylglutaronitrile: between 70% and 95%,
2-Ethylsuccinonitrile: between 5% and 30%,
Adiponitrile: between 0% and 10%,
the remainder to 100% corresponding to various impurities.

5. The process according to claim 1, wherein the compound of formula II or IV results from a renewable material of vegetable origin.

6. The process according to claim 1, wherein R is selected from:
linear or branched alkyl groups,
linear or branched mono-, poly- or perhalogenated alkyl groups,
ether $R_2$—O— or thioether $R_2$—S— groups,
acyloxy or aroyloxy $R_2$—CO—O— groups,
acyl or aroyl $R_2$—CO— groups,
the hydroxyl group,
a halogen atom,
wherein $R_2$ represents a linear or branched alkyl group having from 1 to 6 carbon atoms or the phenyl group.

7. The process according to claim 1, wherein y is equal to 1 and R represents —CO—O—$R_3$, wherein $R_3$ represents an alkyl group having from 1 to 4 carbon atoms in the general formula II or IV.

8. The process according to claim 1, wherein the compound of formula II or IV is 2,5-furandicarboxylic acid, 2,5-tetrahydrofurandicarboxylic acid, 2-furoic acid, 2,5-furandicarboxylic acid monomethyl ester or 2,5-tetrahydrofurandicarboxylic acid monomethyl esters.

9. The process according to claim 1, further comprising recovering, at least the nitrile of formula I or III and, at least the cyclic imide 3-methylglutarimide, by separation of the compounds of the reaction medium.

10. The process according to claim 9, wherein the recovered nitrile is hydrogenated in order to form the corresponding amine.

11. The process according to claim 9, wherein the recovered cyclic imide 3-methylglutarimide is reacted with an alcohol in order to form the corresponding diester.

12. The process according to claim 4, wherein 2-Methylglutaronitrile is between 80% and 85% by weight.

13. The process according to claim 4, wherein 2-Ethylsuccinonitrile is between 8% and 12% by weight.

14. The process according to claim 4, wherein Adiponitrile is between 1% and 5% by weight.

15. The process according to claim 6, wherein the linear or branched alkyl groups have from 1 to 6 carbon atoms.

16. The process according to claim 6, wherein the linear or branched mono-, poly- or perhalogenated alkyl groups have from 1 to 6 carbon atoms and from 1 to 13 halogen atoms.

17. The process according to claim 6, wherein the halogen atom is a fluorine atom.

18. The process according to claim 6, wherein $R_2$ represents a linear or branched alkyl group having from 1 to 4 carbon atoms.

19. The process according to claim 6, wherein the linear or branched alkyl groups have from 1 to 4 carbon atoms.

20. The process according to claim 6, wherein the linear or branched mono-, poly- or perhalogenated alkyl groups have from 1 to 4 carbon atoms and from 1 to 9 halogen atoms.

* * * * *